United States Patent [19]

Garr

[11] 3,961,380
[45] June 8, 1976

[54] BATHTUB APPLIANCE WITH HOT WATER BLADDER AND HEAT CHAMBER

[76] Inventor: Ernest J. Garr, 3587 Powell Drive, Lafayette, Calif. 94549

[22] Filed: May 27, 1975

[21] Appl. No.: 580,953

[52] U.S. Cl. .................................. 4/160; 4/162; 4/163; 128/369; 128/373; 5/365
[51] Int. Cl.² ........................................ A61H 33/12
[58] Field of Search ............ 4/162, 160, 163, 164, 4/185 R, 185 AB, 185 S; 128/369, 373; 5/348 R, 350

[56] References Cited
UNITED STATES PATENTS

| | | | |
|---|---|---|---|
| 1,531,833 | 3/1925 | Bauer | 4/163 |
| 1,943,888 | 1/1934 | Ewald | 128/369 X |
| 2,095,749 | 10/1937 | Kellner | 4/162 |
| 3,292,185 | 12/1966 | Lucian | 4/145 |
| 3,375,534 | 4/1968 | Vieceli | 4/162 |
| 3,581,315 | 6/1971 | Milliner | 4/162 |
| 3,611,448 | 10/1971 | Dudley | 4/162 |
| 3,837,014 | 9/1974 | Sugiyama | 4/162 |

*Primary Examiner*—Henry K Artis
*Attorney, Agent, or Firm*—Flehr, Hohbach, Test, Albritton & Herbert

[57] ABSTRACT

Bathtub appliance having a bladder filled with warm water on which a person can sit or recline, with a flexible cover attached to the bladder forming a heated enclosure for the person's body. An elongated opening is provided in the cover, and fastening means are provided at both ends of the opening whereby the cover can be closed about the neck of the person resting in a plurality of positions. The bladder is filled with water from the bathtub faucet, and means is included for introducing water into the enclosed compartment in which the person rests, if desired.

7 Claims, 3 Drawing Figures

U.S. Patent    June 8, 1976    3,961,380
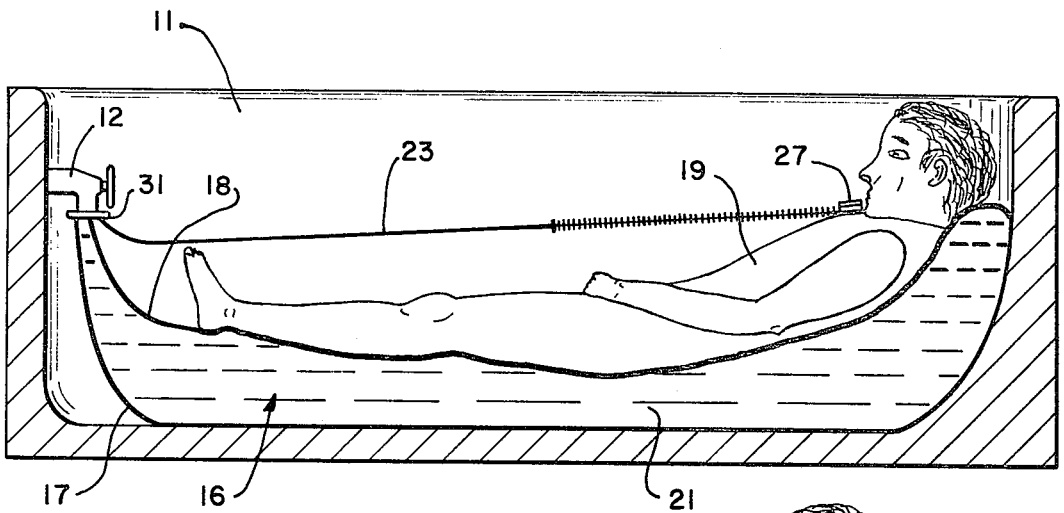
FIG.—1
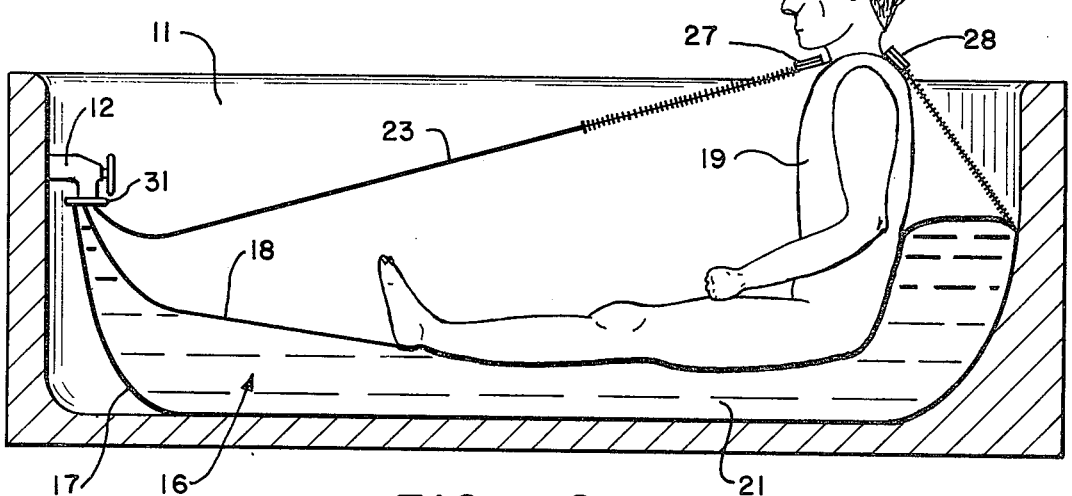
FIG.—2
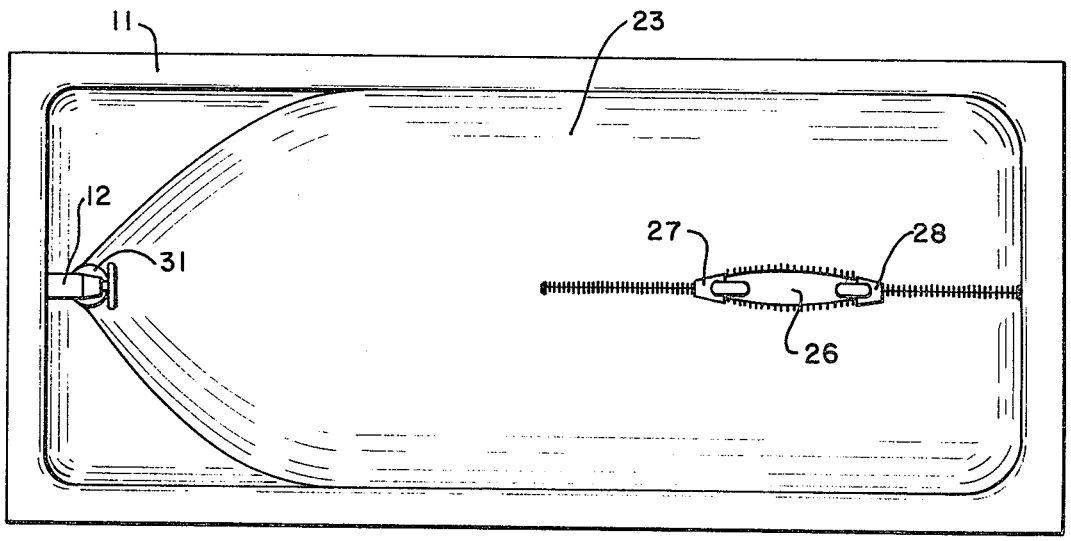
FIG.—3

BATHTUB APPLIANCE WITH HOT WATER BLADDER AND HEAT CHAMBER

BACKGROUND OF THE INVENTION

This invention pertains generally to bathtub appliances and more particularly to a device having a bladder filled with warm water and a flexible cover forming a heated enclosure for a person sitting or reclining upon the bladder.

For many years, appliances such as hot water bottles and heating pads have been used in the treatment of backaches and other discomforts. Such appliances are sometimes awkward to use, and they generally are capable of heating only a small portion of a person's body.

Various appliances have also been provided for use in conventional bathtubs in order to provide steam or vapor baths. These appliances have included supports for holding a person above the water in a tub, with covers for retaining the steam or vapor, and examples of such devices are found in U.S. Pat. Nos. 1,111,094, 2,095,749, 2,504,646 and 3,611,446.

SUMMARY AND OBJECTS OF THE INVENTION

The invention provides a bathtub appliance having a bladder filled with warm water on which a person can sit or recline, with a flexible cover attached to the bladder forming an enclosure for the person's body. An elongated opening is provided in the cover, and fastening means are provided at both ends of the opening whereby the cover can be closed about the neck of the person resting in a plurality of positions. The bladder is filled with water from the bathtub faucet, and means is included for introducing water into the enclosed compartment in which the person rests, if desired.

It is in general an object of the invention to provide a new and improved bathtub appliance.

Another object of the invention is to provide an appliance of the above character having a bladder filled with warm water on which a person can sit or recline.

Another object of the invention is to provide an appliance of the above character having a flexible cover with an elongated opening and fastening means for closing the cover about the neck of a person resting on the bladder.

Additional objects and features of the invention will be apparent from the following description in which the preferred embodiment is set forth in detail in conjunction with the accompanying drawings.

BRIEF DESCRIPTION OF THE DRAWINGS

FIG. 1 is a cross sectional view of one embodiment of a bathtub appliance according to the invention, with a person illustrated in a reclining position on the appliance in a bathtub.

FIG. 2 is a cross sectional view similar to the view of FIG. 1, with the person illustrated in a sitting position.

FIG. 3 is a top plan view of the embodiment of FIGS. 1 and 2.

DESCRIPTION OF THE PREFERRED EMBODIMENT

In the drawings, the invention is illustrated in conjunction with a conventional bathtub 11 having a faucet or spigot 12 through which water of a desired temperature is introduced into the tub.

The appliance comprises a bladder 16 having a lower wall 17 which engages the bottom wall and at least one side wall of the bathtub and an upper wall 18 of sufficient size to receive a person 19 in a sitting or reclining position. A body of water 21 is enclosed within the bladder and cooperates therewith to support the person away from the walls of the tub.

In the preferred embodiment, the bladder is fabricated of a flexible, substantially inelastic material, such as vinyl plastic, and the bladder rests upon the bottom wall and the side wall at one end of the tub. The body of water within the bladder provides floating support for the person resting thereon and maintains the upper and lower bladder walls in a spaced relationship.

A flexible cover 23 is attached to the bladder and overlies the bladder to form an enclosure for the body of the person resting on the bladder. In the preferred embodiment, the cover is also fabricated of a material such as vinyl plastic, and it is of larger area than the upper wall of the bladder. The cover is formed with an elongated longitudinally extending opening 26 having slide fastening means 27, 28 for closing the same. As illustrated, fasteners are provided toward both ends of the opening whereby the opening can be closed about the neck of the person in a plurality of sitting and reclining positions. The slide fasteners can be of suitable know design, and they preferably include operating tabs which are accessible both inside and outside the enclosure.

Means is included for filling either bladder 16 or the enclosure formed by cover 23 with water from faucet 12. This means includes a diverter valve 31 which serves to connect either the bladder or the enclosure in fluid communication with the faucet.

Operation and use of the appliance can be described briefly. It is assumed that the device has been placed in the tub and that valve 31 has been connected to faucet 12. When the bladder is filled with water of a desired temperature, the user positions himself upon the bladder and closes the cover about his neck. If desired, water can also be introduced through faucet 12 and valve 31 into the user's compartment. It is contemplated that the water introduced into the bladder and into the user's compartment will ordinarily be hot water, but the water can be of any desired temperature. The body of water in the bladder will conform closely to the contour of the user's body to provide uniform support for the body throughout the area of contact with the bladder. Heat from the water in the bladder is applied directly to the portion of the body in contact with the bladder, and heat is retained within the enclosure by cover 23. When its use is completed, the appliance can be drained, removed from the tub, and rolled or folded for storage.

The invention has a number of important features and advantages. The water in the bladder conforms closely to the contours of the user's body to provide a very comfortable support and good heat transfer over a substantial portion of the body. The flexible cover retains the heat from the water within the enclosure, and the fasteners at both ends of the opening permit the user to rest in a number of sitting and reclining positions. The appliance is lightweight and flexible and can be removed from the tub and stored when not in use.

It is apparent from the foregoing that a new and improved bathtub appliance has been provided. While only one presently preferred embodiment has been described, as will be apparent to those familiar with the art, certain changes and modifications can be made without departing from the scope of the invention as defined by the following claims.

I claim:

1. In an appliance for use in a bathtub: a bladder fabricated of a flexible material adapted to rest in the lower portion of the bathtub and contain therein a body of water for supporting a person away from the walls of the tub in a sitting or reclining position, and a flexible cover attached to and integral with the bladder forming an enclosure for the body of a person resting on the bladder.

2. The appliance of claim 1 wherein the cover is formed to include an elongated opening with fastening means toward the ends of the opening for closing the same about the neck of a person resting on the bladder.

3. The appliance of claim 1 further including means for connecting the bladder in fluid communication with a faucet in the bathtub whereby the bladder can be filled with water from the faucet.

4. The appliance of claim 1 further including means for connecting the enclosure formed by the cover in fluid communication with a faucet in the bathtub whereby water can be introduced into the enclosure from the faucet.

5. In an appliance for use in a bathtub: a bladder of flexible material having a lower wall engaging the bottom wall and at least one side wall of the bathtub and an upper wall of sufficient size to receive a person in a sitting or reclining position, a body of water enclosed within the bladder for maintaining the upper and lower walls in a spaced relationship with the upper wall conforming to the contour of a person resting on the bladder, and a flexible cover attached to the bladder and cooperating with the upper wall to form an enclosure for the body of the person resting on the bladder.

6. The recliner of claim 5 wherein the cover is formed to include an elongated opening with fastening means toward the ends of the opening for closing the same about the neck of the person resting on the bladder.

7. The recliner of claim 5 wherein the water in the bladder is warm water.

* * * * *